: US009039606B2

United States Patent
Uchiyama et al.

(10) Patent No.: US 9,039,606 B2
(45) Date of Patent: May 26, 2015

(54) ENCAPSULATED MEDICAL DEVICE GUIDANCE SYSTEM, AND A METHOD OF CONTROLLING THE SAME

(75) Inventors: Akio Uchiyama, Yokohama (JP); Atsushi Kimura, Akiruno (JP); Isao Aoki, Sagamihara (JP)

(73) Assignees: OLYMPUS CORPORATION, Tokyo (JP); OLYMPUS MEDICAL SYSTEMS CORP., Tokyo (JP)

( * ) Notice: Subject to any disclaimer, the term of this patent is extended or adjusted under 35 U.S.C. 154(b) by 1472 days.

(21) Appl. No.: 12/146,712

(22) Filed: Jun. 26, 2008

(65) Prior Publication Data
US 2008/0294006 A1 Nov. 27, 2008

Related U.S. Application Data

(63) Continuation of application No. PCT/JP2006/326148, filed on Dec. 27, 2006.

(30) Foreign Application Priority Data

Dec. 27, 2005 (JP) ................................. 2005-376277

(51) Int. Cl.
*A61B 1/04* (2006.01)
*A61B 1/00* (2006.01)
*A61B 19/00* (2006.01)

(52) U.S. Cl.
CPC ............. *A61B 1/041* (2013.01); *A61B 1/00158* (2013.01); *A61B 19/22* (2013.01); *A61B 2019/2253* (2013.01)

(58) Field of Classification Search
None
See application file for complete search history.

(56) References Cited

U.S. PATENT DOCUMENTS

2005/0062562 A1* 3/2005 Ries .................................. 335/1
2005/0216231 A1* 9/2005 Aoki et al. .................... 702/183
(Continued)

FOREIGN PATENT DOCUMENTS

| DE | 10 2007 051 861 A1 | 5/2009 |
| JP | 2003-111720 | 4/2003 |
| JP | 2003-260026 A | 9/2003 |

(Continued)

OTHER PUBLICATIONS

Kothandaraman and Rudramoorthy, Basic Fluid Mechanics, 1999, New Age International (P) Ltd., Publishers, pp. 149-154.*

(Continued)

*Primary Examiner* — Anhtuan T Nguyen
*Assistant Examiner* — Alexandra Newton
(74) *Attorney, Agent, or Firm* — Scully, Scott, Murphy & Presser, P.C.

(57) ABSTRACT

An encapsulated medical device guidance system, and a method of controlling the system, in which a magnetic generator acts on a magnet built into a capsulated medical device, and generates a magnetic field for controlling the position and/or posture of the capsulated medical device, and a control unit has a dynamic torque estimation unit to estimate a dynamic torque to be applied to the encapsulated medical device in a target posture, controls a magnetic field generated from the magnetic field generator so that a magnetic torque generated by the magnetic field generator becomes proportional to a dynamic torque estimated by the dynamic torque estimation unit, and controls the posture of a capsule endoscope by considering gravity applied to the capsule endoscope itself.

12 Claims, 8 Drawing Sheets

(56) References Cited

U.S. PATENT DOCUMENTS

2006/0169293 A1* 8/2006 Yokoi et al. .................. 128/899
2006/0258901 A1* 11/2006 Fujimori et al. ............. 600/101

FOREIGN PATENT DOCUMENTS

| JP | 2004-255174 | | 9/2004 |
| JP | 2004-298560 | | 10/2004 |
| JP | 2005-87737 | | 4/2005 |
| JP | 2005-130943 | A | 5/2005 |
| WO | WO 96/03795 | A1 | 2/1996 |

OTHER PUBLICATIONS

Oteh, Mechanics of Fluids, 2008, AuthorHouse, pp. 65-67.*

Japanese Office Action dated Sep. 13, 2011 from corresponding Japanese Patent Application No. 2007-552971 together with English language translation.

Extended Supplementary European Search Report dated Jan. 28, 2010.

Date-of-receipt stamped letter to establish the date (Feb. 9, 2010) on which the European Search Report was received.

* cited by examiner

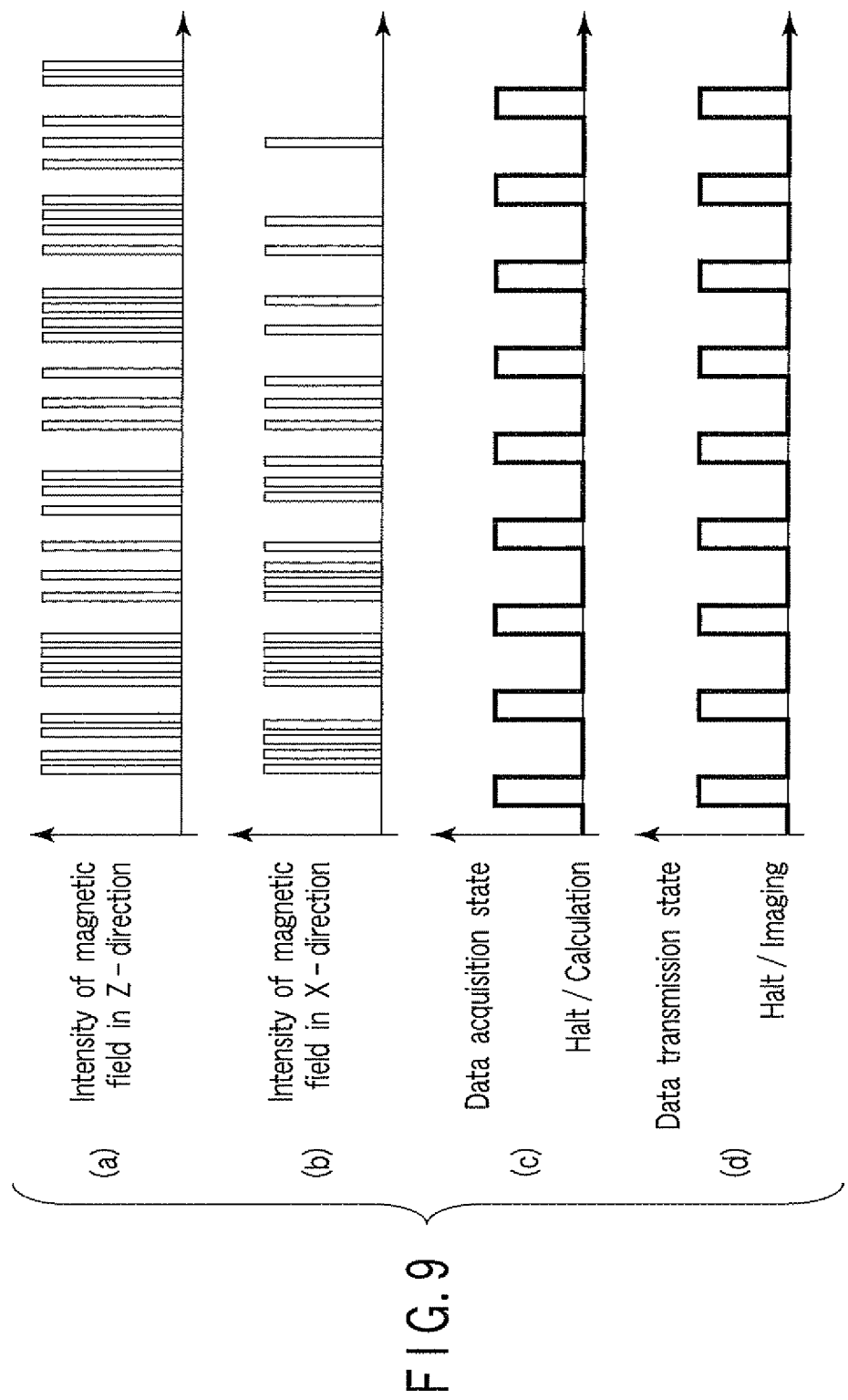
F I G. 9

ENCAPSULATED MEDICAL DEVICE GUIDANCE SYSTEM, AND A METHOD OF CONTROLLING THE SAME

CROSS REFERENCE TO RELATED APPLICATIONS

This is a Continuation Application of PCT Application No. PCT/JP2006/326148, filed Dec. 27, 2006, which was published under PCT Article 21(2) in Japanese.

This application is based upon and claims the benefit of priority from prior Japanese Patent Application No. 2005-376277, filed Dec. 27, 2005, the entire contents of which are incorporated herein by reference.

BACKGROUND OF THE INVENTION

1. Field of the Invention

The present invention relates to a guidance system for an encapsulated medical device inserted into an intracavital for obtaining internal biological information, and a method of controlling the same.

2. Description of the Related Art

Among conventional medical devices for obtaining internal biological information, there is a known encapsulated medical device which periodically transmits image information while moving in an intracavital.

As such an encapsulated medical device, a medical device guidance system configured to be magnetically guided has been proposed as disclosed in Jpn. Pat. Appln. KOKAI Publication No. 2004-255174. In this proposal, a medical device guidance system is inserted in a intracavital a capsule unit provided with spiral projections around the perimeter contains a magnet magnetized in the direction perpendicular to the longitudinal direction, and the advancing direction of the capsule unit can be smoothly changed by a magnetic field generated by a magnetic field control unit and a rotational magnetic field generator based on operating instructions. By freely changing the capsule unit advancing direction, the direction of the capsule unit can be changed upon imaging, and an image of a desired part of the intracavital can be acquired.

Jpn. Pat. Appln. KOKAI Publication No. 2003-111720 proposes an apparatus, which images an inspection area in the body of a patient by generating a 3D gradient magnetic field for determining the positions of a carrier, which contains a linear magnet and a measuring instrument or a sample collecting device, and functions as a robot to move freely in the body of a patient, by moving it in the body under remote control.

BRIEF SUMMARY OF THE INVENTION

A first encapsulated medical device guidance system according to an embodiment of the invention has an internal biological information acquisition unit to acquire internal biological information; a communication unit to output the acquired internal biological information to the outside as an output signal; an encapsulated medical device having a magnet; a magnetic field generator which acts on the magnet, and generates a magnetic field for controlling at least one of the position and posture of the encapsulated medical device; and a control unit to control the magnetic field generator, wherein the control unit has a dynamic torque estimation unit to estimate a dynamic torque to be applied to the encapsulated medical device in a target posture, and controls a magnetic field generated from the magnetic field generator so that a magnetic torque generated by applying a magnetic field generated by the magnetic field generator to the magnet becomes substantially proportional to a dynamic torque estimated by the dynamic torque estimation unit.

A second encapsulated medical device guidance system comprises an internal biological information acquisition unit to acquire internal biological information; a communication unit to output the acquired internal biological information to the outside as an output signal; an encapsulated medical device having a magnet; a magnetic field generator which acts on the magnet, and generates a magnetic field for controlling at least one of the position and posture of the encapsulated medical device; and a control unit to control the magnetic field generator, wherein the control unit controls the magnetic field generator which generates a magnetic field in a direction different from a desired direction of the encapsulated medical device generated by acting on a magnet, and controls the encapsulated medical device to face a desired direction, without being influenced by gravity.

As a third embodiment of the invention, there is provided a method of guiding an encapsulated medical device, comprising a step of setting a target posture of an encapsulated medical device, a step of determining a dynamic torque to be applied to the encapsulated medical device, a step of calculating a magnetic field for generating a magnetic torque proportional to the dynamic torque, in a target posture of the encapsulated medical device, and a step of generating the calculated magnetic field in the vicinity of the encapsulated medical device.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 9 is a timing chart for explaining a second method of controlling an encapsulated medical device guidance system;

DETAILED DESCRIPTION OF THE INVENTION

Hereinafter, embodiments of the invention will be explained in detail with reference to the accompanying drawings.

Figure 1:
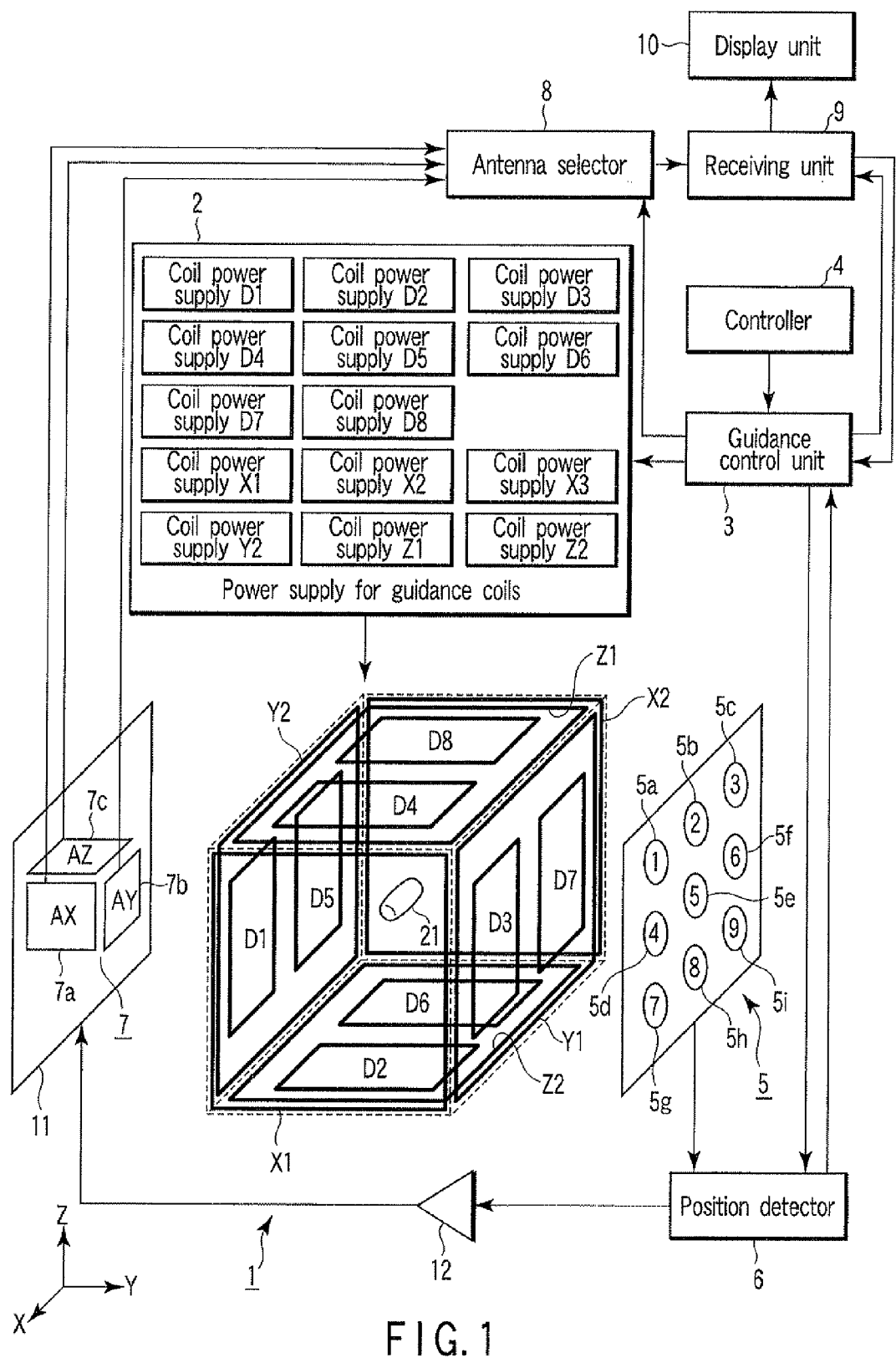
FIG. 1 is a diagram showing the configuration of an encapsulated medical device guidance system according to an embodiment of the invention.

An explanation will be given on an encapsulated medical device guidance system according to one embodiment of the invention shown in FIG. 1. This encapsulated medical device guidance system is largely divided into an encapsulated medical device 21 shown in FIGS. 2 to 6, and a magnetic guidance unit 1 which generates a magnetic field for guiding a capsule endoscope. As an encapsulated medical device in this embodiment, a capsule endoscope 21 is taken and explained as an example.

The magnetic guidance unit 1 mainly comprises a guidance coil group (X1, X2, Y1, Y2, Z1, Z2, D1, D2, D3, D4, D5, D6, D7, DR), a power supply 2 for guidance coils, a guidance control unit 3, a controller 4, a sense coil unit 5 (5a-5i), a position detector 6, a receiving antenna unit 7 (7a, 7b, 7c), an antenna selector 8, a receiving unit 9, a display unit 10, a drive coil 11, and a drive coil driver 12.

Each of fourteen guidance coils X1, X2, Y1, Y2, Z1, Z2 and D1-D8 has an air-core electromagnet, and forms an induction magnetic field generator. In this embodiment, the guidance coils are arranged on each side of a rectangular parallelepiped. As shown by the arrow in FIG. 1, the direction of moving the capsule endoscope 21 forward and backward (or the direction of moving a human body to be examined) is assumed to be an X-axis direction, and the direction horizontally perpendicular to the X-axis is assumed to be a Y-axis direction, and a vertical (gravity) direction vertically perpendicular to the X-axis is assumed be a Z-axis direction.

In these axis directions, the guidance coils X1 and X2 are placed oppositely around the surfaces of front and rear sides, forming magnetic lines of force in the X-axis direction, and becoming vertical to the X-axis direction. The guidance coil X1 side is assumed to be front, and the guidance coil X2 side is assumed to be rear. Moving from the guidance coil X2 to the guidance coil X1 is assumed to be moving forward, and moving in the reverse direction is assumed to be moving backward.

The guidance coils Y1 and Y2 are placed oppositely around the surfaces of both sides, forming magnetic lines of force in the Y-axis direction, and becoming vertical to the Y-axis direction. In one of these sides, two guidance coils D3 and D7 are arranged within the guidance coil Y1 so as to divide the plane into two parts, and in the other opposite side, two guidance coils D1 and D5 are arranged within the guidance coil Y2 so as to divide the plane into two parts.

Similarly, the guidance coils Z1 and Z2 are placed oppositely around the top and bottom planes with respect to the Z-axis direction, forming magnetic lines of force in the Z-axis direction. In the top plane, two guidance coils D4 and D8 are arranged within the guidance coil ZS so as to divide the plane into two parts, and in the opposite bottom plane, two guidance coils D2 and D6 are arranged within the guidance coil Z2 so as to divide the plane into two parts. The guidance coil Z1 side is assumed to be top, and the guidance coil Z2 side is assumed to be bottom. Moving from the guidance coil Z2 to the guidance coil Z1 is assumed to be moving upward, and moving in the reverse direction is assumed to be moving downward.

An alternating magnetic field formed by the drive coil 11 acts on the magnetic induction coil 31 and generates an induction current, and a magnetic field is generated from the magnetic induction coil. This alternating magnetic field includes one or more frequency components close to a resonance frequency generated by a coil (magnetic induction coil 31) and capacitor 33 described later provided in the capsule endoscope 21.

The generated induction magnetic field is detected by the sense coils 5a-5i, a signal including the position information is generated, and the signal is sent to the position detector 6. Based on this signal, the position detector calculates the position and posture information in the capsule endoscope 21. The position and posture information is sent to the guidance control unit 3, and used for calculation of a magnetic field to be generated by the guidance coil group.

The group of guidance coils X1, X2, Y1, Y2, Z1, Z2, and D1-D8 is a first magnetic gradient generating means, which generates a magnetic gradient (a first magnetic gradient) to be applied to the magnet in the capsule endoscope 21, and pulls the endoscope in a desired direction by moving in the longitudinal, horizontal and vertical directions.

The guidance coil Z1 eliminates the influence of gravity when pulling the capsule endoscope 21 in a desired direction by moving up the endoscope by the above-mentioned guidance coil group, by generating a magnetic gradient (a second magnetic gradient) to be applied to the magnet in the capsule endoscope 21 to cancel the force of moving down the endoscope moved by the gravity. The guidance coils D4 and D8 can also generate the same force as the guidance coil Z1. The guidance coil Z1 is a second magnetic gradient generating means to eliminate the influence of gravity when moving the endoscope in a desired direction. On the other hand, the guidance coil Z2 eliminates the influence of buoyancy when pulling the capsule endoscope 21 in a desired direction by moving down the endoscope by the above-mentioned guidance coil group, by generating a magnetic field to be applied to the magnet in the capsule endoscope 21 to cancel the force of moving up the endoscope moved by the buoyancy. The guidance coils D2 and D6 can also generate the same force as the guidance coil Z1.

Concretely, the oppositely placed guidance coils X1 and X2, Y1 and Y2, and Z1 and Z2 generate a uniform magnetic field within the space surrounded by these guidance coils when a magnetic field is generated in the same direction, and forms an oblique magnetic field when a magnetic field is generated in the opposite direction. The coils D1-D8 can form a highly uniform magnetic field or a gradient magnetic field by driving appropriately. Therefore, by controlling these fourteen guidance coils, it is possible to generate a magnetic field having desired intensity and gradient within a desired space.

In such arrangement of the guidance coil group, in addition to moving the capsule endoscope 21 in the longitudinal, horizontal and vertical directions, it is possible to incline the endoscope to a position rising to the front, for example, by generating a magnetic field to tilt the distal end side up and proximal end side down, by combining the guidance coils X1, X2, Y1, Y2, Z1, Z2 and D1-D8.

These guidance coils are connected to the power supply 2 for guidance coils driven individually. The power supply 2 for guidance coils is controlled by the instruction from the guidance control unit 3, appropriately supplies power to a guidance coil necessary for generating a magnetic field, and generates a desired magnetic field in a desired space.

In this embodiment, a position detection system (a position detecting means) for detecting information about a position (a position in pace) of the capsule endoscope 21 comprises a drive coil 11 for generating an induction magnetic field in the coil provided in the capsule endoscope 21, a sense coil group 5 for detecting the induction magnetic field generated in the capsule endoscope 21, a position detector 6 for generating the information about a position of the capsule endoscope 21 (the position in a three-dimensional space and the direction of the capsule endoscope) from the signal based on the induction magnetic field received by the sense coil group 5, and a drive coil driver 12 for driving the drive coil 11 according to an instruction from the position detector 6.

Nine sense amplifiers 5a-5i constituting the sense coil group 5 are arranged to be parallel to the side provided with the guidance coil Y1 and uniform in a plane, so that the correct position and posture of the capsule endoscope 21 can be obtained. In this embodiment, the position related to the Z-axis is detected by providing a pair of oppositely placed sense coil set S and a drive coil 11. However, for detecting a three-dimensional position and posture, it is preferable to provide the pair on each of two crossing planes, for example, top and side planes. To increase the detection accuracy, a little more number of sense coils is preferable.

The position detector 6 receives an instruction to specify a timing of detecting the information about a position from the guidance control unit 3, and drives the drive coil driver 12 based on the instruction. The drive coil driver 12 generates a magnetic field by supplying an AC current to the drive coil 11, and generates an induction magnetic field in the capsule endoscope 21 in the magnetic field. Each sense coil of the sense coil group 5 detects a signal based on the induction magnetic field generated from the capsule endoscope 21, and outputs it to the position detector 6. The position detector 6 generates the position and posture information of the capsule endoscope 21 from the signal based on the induction magnetic field, and outputs it to the guidance control unit 3. The guidance control unit 3 determines a desired moving direction considering the position and posture information of the capsule endoscope 21 from the position detector 6, and instructs the power supply 2 for guidance coils to generate a magnetic field suitable for moving in the desired moving direction. The power supply 2 for guidance coils feeds a current to the guidance coils X1, X2, Y1, Y2, Z1, Z2 and D1-D8 according to the instruction from the guidance control unit 3. Therefore, a magnetic field suitable for that moving is generated by the guidance coils, and the capsule endoscope 21 can be smoothly guided.

The controller 4 is an input unit, which instructs the advancing direction and inclination of the capsule endoscope 21, by the operation of an input device by the operator, for example, tilting a joystick to a desired direction. In addition to a joystick, buttons arranged to instruct all directions, a touch panel, or a line-of-sight input unit is available as a means to operate the controller 4.

The guidance control unit 3 receives an instruction signal from the controller 4, position and posture information from the position detector 6, and signals related to the driving states of the guidance coils from the receiving unit 9, calculates a magnetic force (a magnetic field) for moving the capsule endoscope 21 to a desired position, determines magnetic forces generated by the guidance coils X1, X2, Y1, Y2, Z1, Z2 and D1-D8 for generating the magnetic force, and sends an instruction to the power supply for each guidance coil.

Further, the guidance control unit 3 stops generation of a magnetic field during a communication period over which the image data acquired by the capsule endoscope 21 is sent to the receiving unit 9. At the same time, during this communication period, the position detector 6 drives the drive coil 11 based on the instruction from the guidance control unit, and acquires the position information from the sense coil group 5.

Three receiving antennas 7 are connected to the receiving unit through an antenna selector 8 for selecting the antennas. These receiving antennas 7 consist of a receiving antenna 7a (AX) for receiving communication data (internal biological information including image data) from the X-axis direction, a receiving antenna 7b (AY) for receiving internal biological information from the Y-axis direction, and a receiving antenna 7c (AZ) for receiving internal biological information from the Z-axis direction. The receiving antennas 7 can detect internal biological information in three axial directions.

The antenna selector 9 selects the antennas 7a, 7b and 7c to be used for communication. The antenna selector 8 receives the intensity, direction and gradient of a magnetic field generated by the guidance coil group at the position of each antenna, identifies a receiving antenna influenced minimum by the magnetic field, and selects that receiving antenna. By selecting such a receiving antenna 7, the communication between the receiving unit 9 and capsule endoscope 21 can be stabilized.

The receiving unit 9 sends the guidance control unit 3 the timing of receiving internal biological information from the capsule endoscope 21. As described above, the guidance control unit 3 stops generation of an induction magnetic field by the guidance coil set and drive coil 11, during the communication period for sending internal biological information (image data). Due to this stoppage, the receiving unit can receive the internal biological information from the capsule endoscope 21 without being influenced by an induction magnetic field. By this stop period, the communication period does not overlap the moving operation and position detection period, and it is possible to eliminate a noise in the internal biological information caused by an induction magnetic field, or an influence of an induction magnetic field on the receiving antenna.

Therefore, this stop operation is useful in the point that image data is not influenced by a noise, and the receiving antenna is prevented from being influenced by an induction magnetic field, when a magnetic field generated close to the capsule endoscope 21 has high intensity and much gradient, or when a magnetic field generated close the receiving antenna 7 has high intensity and much gradient. Further, even if a magnetic field generated by the guidance coil has high intensity, the position detector 6 can be operated normally.

The display unit 10 consists of a liquid crystal display, and displays an image generated by the receiving unit 9 and shot by the capsule endoscope 21. When the image is displayed, the data such as imaging situation related to the displayed image may be displayed on the screen together with the image.

An explanation will now be given on first to fifth configuration examples in the capsule endoscope 21 according to this embodiment with reference to FIG. 2-FIG. 5.

Figure 2:
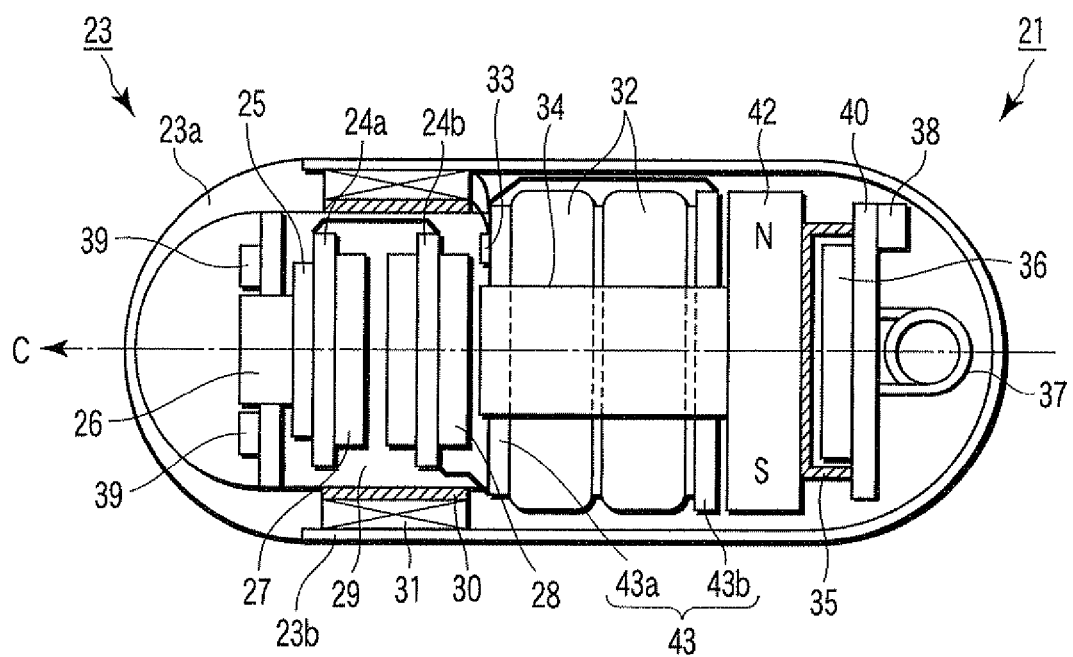
FIG. 2 is a sectional view showing the configuration of a first capsule endoscope according to the embodiment.

FIG. 2 shows the sectional view showing the configuration of a first capsule endoscope according to the embodiment.

A capsule case 23 of the first capsule endoscope 21 comprises of a transparent semiround distal end case 23a placed in the front end side, and a cylindrical proximal end case 23b with a semiround rear end passing infrared rays. The capsule case 23 contains a capsule endoscope described later, and is enclosed watertight. The capsule endoscope 21 advances in the cylinder axial direction indicated by C in FIG. 2.

An explanation will be given on the capsule endoscope itself.

A main body of the capsule endoscope is largely divided into an imaging unit to image the inner wall surface of a passage in a intracavital of a patient, a power supply unit to drive the imaging unit, an induction magnetic field generator to generate an induction magnetic field by the above-mentioned drive coil 11, a magnet to drive the capsule endoscope 21, and a transmission unit to transmit internal biological information including acquired image data to the receiving antenna 7.

The imaging unit comprises imaging optics 26 having a fixed-focus lens, an imaging element 25 consisting of CMOS or CCD mounted on an imaging side substrate 24a, an illumination unit 39 consisting of a light controllable LED provided close to the imaging optics 26, and an image processing circuit 27 to perform predetermined image processing for an image signal from the imaging element 25 mounted on the imaging side substrate 24a in the rear side of the imaging element 25. The imaging side substrate 24a, power supply side substrate 24b, and front side substrate 43 for a battery are sealed with adhesive as a single unit 29 fixed with an adhesive.

The power supply unit comprises a small battery 32 consisting of a button battery, a pair of substrate 43 (43a and 43b) for a battery provided with a not-shown power supply terminal to draw power from the small battery 32, a heat-shrink tube 34 to fix the small battery 32 just like holding by the battery substrate, a power supply side substrate 24b whose circuit wiring is electrically connected to the circuit wiring of the imaging side substrate 24 by a flexible substrate, and a power supply circuit 28 provided on the power supply side substrate 24b and powered by the small battery 32.

The magnetic field generator comprises a magnet 30 provided on the perimeter of the adhesive fixed unit 29, a magnetic induction coil 31 provided through the magnet 30, and a capacitor 33 provided on the substrate for a battery in the front end side, composing a CL resonance circuit together with the magnetic induction coil 31.

The magnetic induction coil 31 is shaped like a ring with a maximum outside diameter a little smaller than the inside diameter of the capsule case 23. The magnet 30 converges an external magnetic field in the magnetic induction coil 31. As a magnet 30, a material with high saturation magnetic flux density and permeability, such as amorphous magnetic substance (magnet) and fine med (HITACHI KINZOKU), is suitable. Use of material shaped like a thin film provides an effect of reducing the volume of magnetic substance (magnet) when placed in a capsule endoscope.

A circular drive magnet 42 is placed on the rear substrate 43b for a battery. As a material of the magnet 42, a neodymium cobalt is suitable, but not limited to this material. The magnet 42 has an N-pole magnetized upward and an S-pole magnetized downward, so that the direction of magnetic lines of force becomes along the Z-axis direction. By setting the polarity as above, the capsule endoscope 21 is always directed to a predetermined direction with respect to the guidance coil group of the magnetic guidance unit 1. Therefore, the top and bottom of an obtained image can be absolutely determined.

The transmission unit comprises a communication circuit 36 mounted on the rear side (the magnet 42 side) of a substrate 40 for transmission, an antenna 37 placed on the front surface side (the proximal end case 23b), a shielding part 35 to cover the exposed communication circuit 36 and to shield a magnetic force of the magnet 42, and an optical switch 38 which is mounted on the substrate 40 for transmission on the side provided with the antenna 27, and turns on/off the capsule endoscope.

In such arrangement, the magnetizing direction of the magnet 42 and the direction of the antenna 37 connected to the transmission circuit 36 are determined by changing the angle by 90 degrees. This is done for establishing the condition that the magnetic field generated by the magnet 42 enters at an angle displaced 90 degrees from the direction of the antenna 37. Therefore, the influence of the magnetic field from the magnet 42 upon the antenna 37 is reduced to minimum.

The shielding part 35 is made of magnetic material, and has an effect to absorb the magnetic field close to the antenna 37. Therefore, the intensity of the magnetic field applied to the antenna 37 can be reduced, and the influence of the magnetic field on the radio communication between the transmission circuit 36 and antenna 37 can be decreased, and stable radio communication can be realized.

The optical switch 38 is sensitive to infrared rays. The proximal end case 23b of the capsule case 23 is made of material to pass infrared rays (in the wavelength sensed by the optical switch) in at least the part close to the optical switch. When infrared rays are applied to the optical switch 38 from a not-shown infrared rays emitter, the optical switch turns on, power is supplied from the small battery 32 through the power supply circuit, and imaging and transmission are started. The circuit of the optical switch 38 is configured to permit a toggle operation. Once infrared rays are applied, the capsule endoscope is kept on. It is permitted to add a configuration, which turns off the endoscope when infrared rays are applied in the on state.

By the configuration to cover the communication circuit 36 by the shielding part 35, the influence of the strong magnetic field of the magnet 42 to the transmission circuit and radio circuit (e.g., a noise is superposed, or a communicable distance is reduced) can be reduced. Therefore, clear image data with less noise can be sent to the receiving unit 9.

Figure 3:
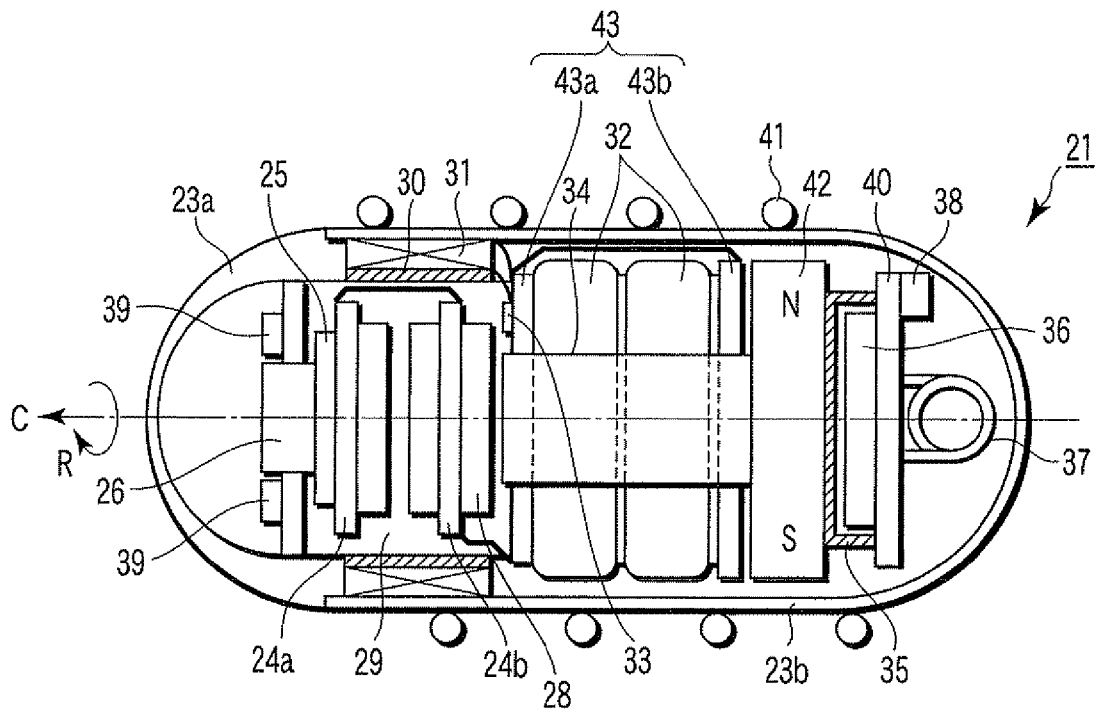
FIG. 3 is a sectional view showing the configuration of a second capsule endoscope according to the embodiment.

FIG. 3 is a sectional view showing the configuration of a second capsule endoscope according to the embodiment.

The second capsule endoscope is provided with a spiral part 25 formed by winding a wire with a circular cross section, on the perimeter of the capsule case 23, unlike the first capsule endoscope. The other parts are the same as the first capsule endoscope, and given the same reference numbers, and an explanation on these parts will be omitted.

In this configuration, the power supply 2 for guidance coils impresses drive voltage to a guidance coil group, and generates the rotating magnetic field to the second capsule endoscope, and the second capsule endoscope 21 is rotated about the axis C in the direction R as shown in FIG. 3.

The second capsule endoscope 21 is moved forward or backward along the axis C, according to the direction of rotating the spiral part 25. Further, as it is possible to rotate the second capsule endoscope 21 as tilted the capsule endoscope can be moved forward or backward in the titled direction. The second capsule endoscope configured as above provides the same function and effect as the first capsule endoscope.

Figure 4:
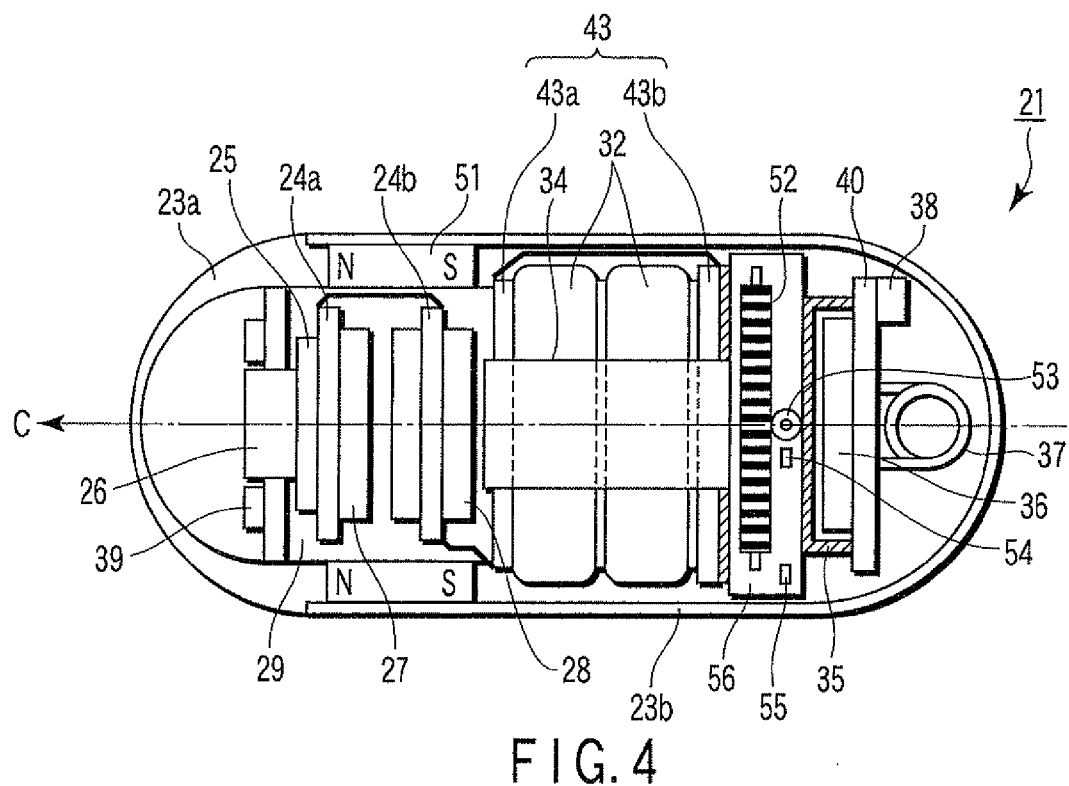
FIG. 4 is a sectional view showing the configuration of a third capsule endoscope according to the embodiment.

FIG. 4 is a sectional view showing the configuration of a third capsule endoscope according to the embodiment.

The third capsule endoscope is configured by replacing the positions of the magnet 42 and magnetic induction coil 31 in the first capsule endoscope. The other parts are the same as the first capsule endoscope, and given the same reference numbers, and an explanation on these parts will be omitted.

Unlike the ring-shaped magnetic induction coil 31 in the first capsule endoscope, two linear stick-shaped induction coils 52 and 53 are crossed in the third capsule endoscope. FIG. 4 shows an example of configuration in which the induction coils 52 and 53 are placed in the directions of axes Z and Y. In the vicinity of the induction coils 52 and 53, capacitors 54 and 55 are placed to connect both ends of the induction coils for forming a LC resonance circuit, and adjusted to obtain a different resonance frequency. The crossed induction coils 52 and 53 generate an induction magnetic field by the magnetic field formed by the drive coil 11. As the induction coils 52 and 53 are vertical to the axis C and faced in different directions, the direction of the axis C (i.e., the capsule endoscope advancing direction) can be detected by obtaining the direction of each induction coil by a respective resonance frequency. Further, in the third capsule endoscope, a magnet 51 is arranged along the longitudinal axis (in the direction of the axis C) of the endoscope (with the N-pole set forward and S-pole set backward). Instead of the circular magnet 42 in the first capsule endoscope, a ring-shaped magnet or a barrel-shaped arrangement of stick magnets is provided on the perimeter of the bond fixed part 29. The third capsule endoscope configured as above can provide the same function and effect as the first capsule endoscope.

Figure 5:
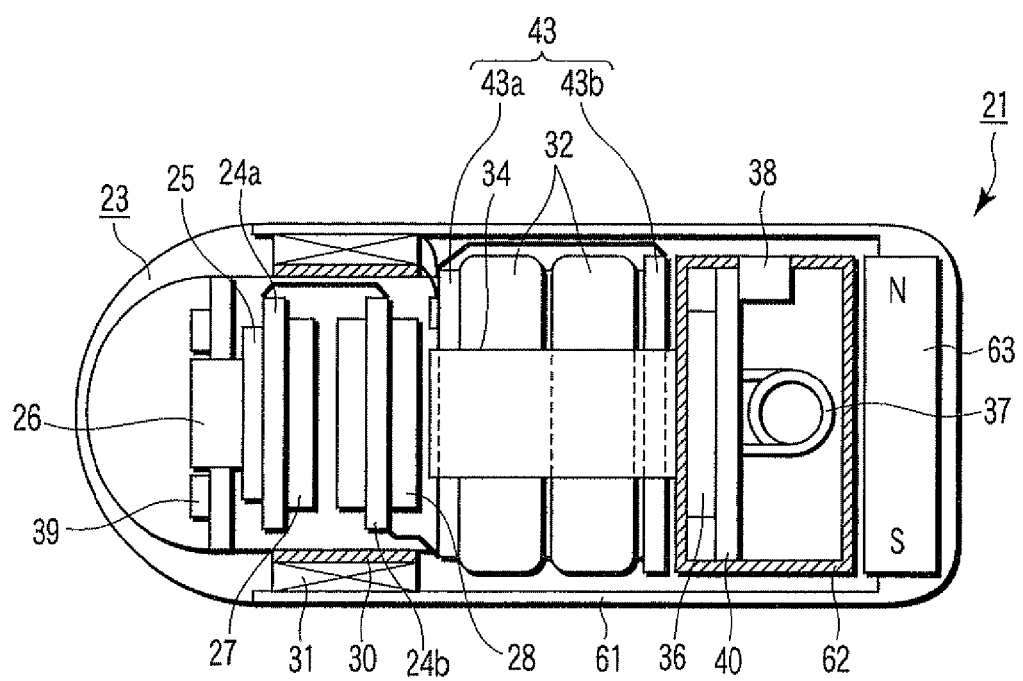
FIG. 5 is a sectional view showing the configuration of a fourth capsule endoscope according to the embodiment.

FIG. 5 is a sectional view showing the configuration of a fourth capsule endoscope according to the embodiment.

The fourth capsule endoscope is configured by replacing the magnet 42, transmission circuit 36 and antenna 37 in the first capsule endoscope. The other parts are the same as the first capsule endoscope, and given the same reference numbers, and an explanation on these parts will be omitted.

In the fourth capsule endoscope, the transmission circuit 36 and antenna 37 are enclosed by the shielding part 62, except the electromagnetic wave emitting direction of the antenna 37, a window for an optical switch is opened, and the optical switch 38 is placed there. A plurality of optical switch 38 may provided in different directions. The shielding part is provided adjacent to the substrate 43b for a battery, and a magnet 63 equivalent to the magnet 42 in the first capsule endoscope is provided in the rear of the substrate. A proximal end case 61 of the capsule case 23 is shaped not semiround, but flat in the rear end. The rear end may be shaped semiround.

The fourth capsule endoscope configured as above can provide the same function and effect as the first capsule endoscope. Further, with this configuration, the magnetic lines of force close to the antenna 37 can be decreased in the intensity by penetrating through the shielding part 62. Therefore, deterioration of transmission performance can be prevented by reducing the influence of the magnetic field generated by the magnet 63 on the antenna 37. A magnetic substance as a shielding member is provided on the substrate by using of a thin film forming technique such as evaporating or sputtering. By this composition, the amount of the magnetic flux which enters in a substrate can be decreased. Therefore, the circuit formed in the capsule endoscope 21 can be prevented from malfunctioning due to an ill effect of a magnetic field of a magnet and induction coil.

Figure 6:
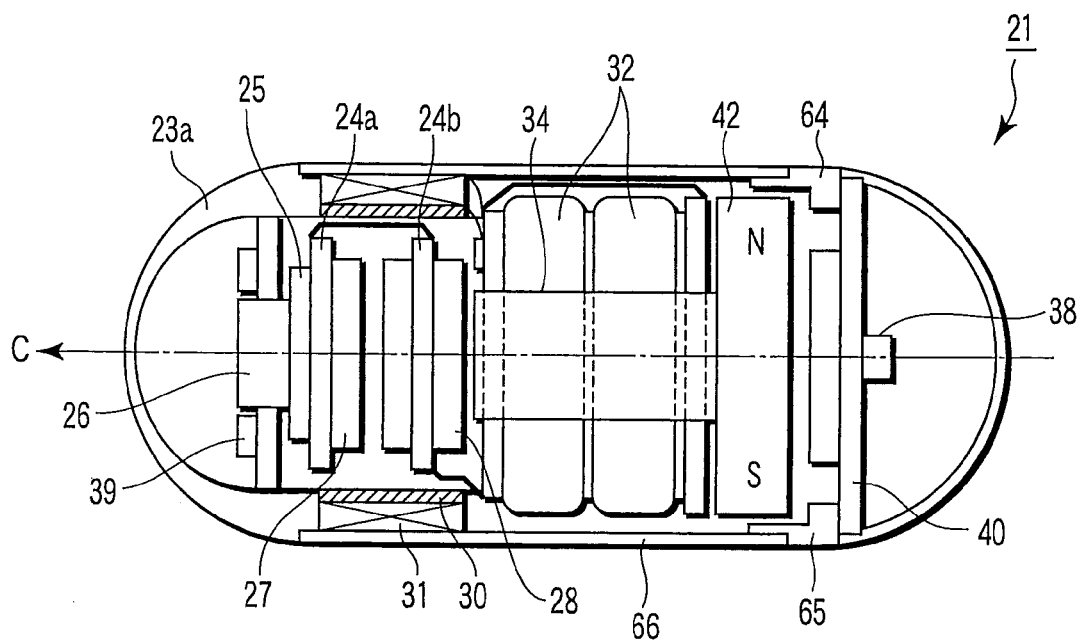
FIG. 6 is a sectional view showing the configuration of a fifth capsule endoscope according to the embodiment.

FIG. 6 is a sectional view showing the configuration of a fifth capsule endoscope according to the embodiment.

In the first capsule endoscope, the internal biological information (image data) is transmitted wirelessly (by radio waves) by using the communication circuit 36 and antenna 37. The fifth capsule endoscope uses a so-called electric field communication system. Namely, electrodes 64 and 65 exposed to the capsule is case surface are provided, a current signal as internal biological information is flowed between the electrodes through a intracavital tissue to be examined, thereby generating an electric field in a living organism, and the internal biological information is received by an electric field sensor fit to the body surface of a patient, instead of the receiving antenna. The other parts are the same as the first capsule endoscope, and given the same reference numbers, and an explanation on these parts will be omitted.

With this configuration, radio waves are not used as a communication medium, an ill effect on the receiving unit and transmission line is eliminated, a noise is hardly superposed, and a stable clear image is obtained, in addition to the function and effect obtained by the first capsule endoscope.

Further, the communication circuit and antenna can be omitted, the configuration becomes simple, and the capsule case can be miniaturized furthermore. By providing a speaker in the transmission circuit and connecting a microphone to the receiving unit, the same function and effect can be obtained by communication using a sound wave.

Now, an explanation will be given on a first method of controlling an encapsulated medical device guidance system configured as described above.

Figure 7:
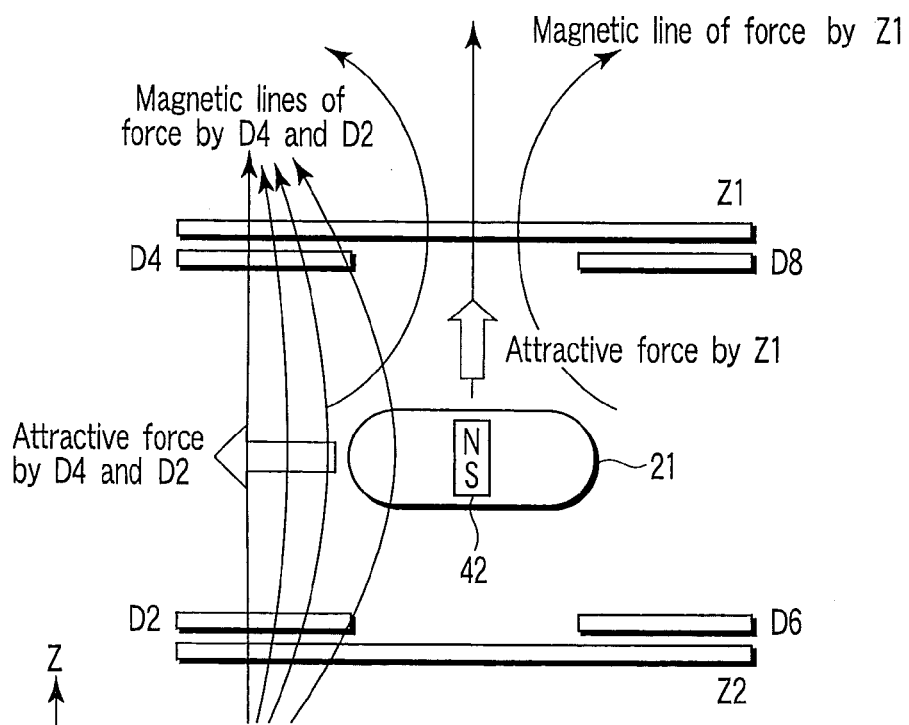
FIG. 7 is a view showing an example of a magnetic field viewed from the Y-axis direction related to guidance, with respect to the first capsule endoscope.

FIG. 7 is a view showing an example of magnetic lines of force in a magnetic field viewed from the Y-axis direction upon guidance, with respect to the first capsule endoscope shown in FIG. 2. This magnetic field is formed in a space surrounded by the guidance coils Z1, Z2, D2, D4, D6 and D8. The capsule endoscope is placed in this space with the distal end facing the direction from the guidance coil X2 to guidance coil X1 (in the X-axis direction) shown in FIG. 6.

In this magnetic field, the guidance coil Z1 generates a magnetic force upward in the Z-axis direction as shown in the drawing. The capsule endoscope 21 generates a magnetic field with the intensity weak in the lower direction (the guidance coil Z2 side) and strong in the upper direction. In the space having such a magnetic gradient, the magnet 42 in the capsule endoscope 21 is given an attractive force in the direction of a strong magnetic field, i.e., upward (called here an upward attractive force).

Receiving the upward attractive force, the capsule endoscope 21 is moved up in the space. By controlling the strength of the upward attractive force by the guidance control unit 3, it is possible to make the state that gravity applied to the capsule endoscope 21 is cancelled. At this time, a magnetic field is formed in the guidance coils D2 and D4 as shown in FIG. 7, and a pulling force for moving forward is generated. Therefore, when the magnetic fields of the guidance coils D2 and D4 are added on the magnetic field of the guidance coil Z1, the capsule endoscope 21 is moved forward while canceling the gravity applied to the endoscope itself.

Namely, in the prior art, the capsule endoscope 21 is moved with its own weight (the mass of the capsule endoscope× acceleration of gravity) put on the intracavital tissue. In contrast, in this embodiment, as the capsule endoscope 21 is reduced in its own weight, and moved in the state that a reaction force is weakened by viscosity, the endoscope can be equally moved even by a magnetic field with a lower intensity. However, if this upward attractive force is excessively applied, the capsule endoscope 21 is unnecessarily floated from the intracavital tissue. Once the capsule endoscope 21 is floated from the intracavital tissue, the capsule endoscope comes close to the guidance coil Z1, the attractive force is weakened furthermore, and the capsule endoscope is suddenly attracted to the guidance coil Z1 and may be floated over the level desired by the user.

By controlling as indicated in the timing chart of FIG. 8(a)-(e), the capsule endoscope is moved while preventing such floating, and communication of internal biological information can be stably performed. FIG. 8(a) shows the intensity and generation timing of a magnetic field generated by the guidance coil Z1 to generate an upward attractive force in the Z-axis direction. FIG. 8(b) shows the intensity and generation timing of a magnetic field generated by the guidance coils D2 and D4 to generate a pulling force in the X-axis direction. FIG. 8(c) shows the timing for the position detector 6 to get signals (position and posture information signals) based on the induction magnetic field, from each sense coil 5. FIG. 8(d) shows the timing of imaging internal biological information, and the timing of transmission and halt of transmission of internal biological information from the capsule endoscope 21 to the receiving unit 9. FIG. 8(e) shows the positions of the intracavital surface and endoscope in the Z-axis direction.

Figure 8:
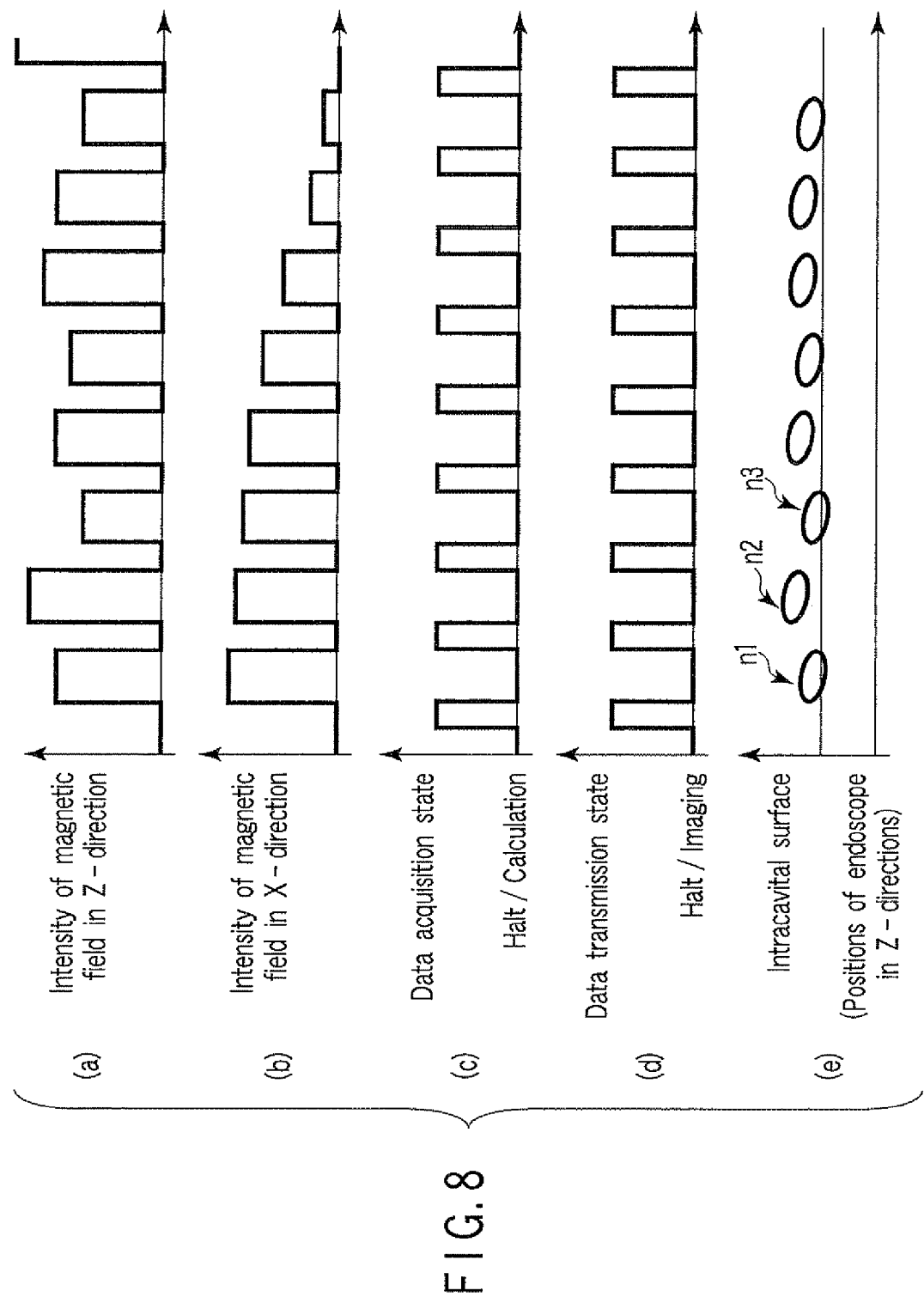
FIG. 8 is a timing chart for explaining a first method of controlling an encapsulated medical device guidance system.

In this embodiment, the operation timing shown in FIG. 8 is set on the basis of the timing of imaging and transmitting image data by the capsule endoscope 21. The timing is not to be limited to this, and may be set as appropriate.

First, the position of the capsule endoscope 21 is detected. When the position is capsule endoscope 21 sinks below the intracavital surface (n1 in FIG. 8(e)) and the magnetic field intensity is lower than a target value, the magnetic field intensity of the guidance coil Z1 is increased to raise the capsule endoscope (to n2) at the next timing. At this time, if the capsule endoscope 21 is excessively raised, the intensity of generated magnetic field is lowered (n3) at the next timing. The relationship between the positions of the intracavital surface and capsule endoscope 21 in the Z-axis direction shown in FIG. 8(e) is conceptual, and actually, the capsule endoscope 21 substantially contacts the intracavital surface, and its weight is not substantially put on the intracavital surface (the endoscope does not sink by its own weight).

At this time, an upward magnetic field in the z-direction as shown in FIG. 7 is generated in the guidance coils D2 and D4. This magnetic field increases the gradient in the direction from the guidance coil X2 to the guidance coil X1, and becomes a pulling force for the capsule endoscope 21 to be pulled forward along the X-axis direction. Therefore, the capsule endoscope 21 is pulled forward by the guidance coils D2 and D4 with the gravity cancelled by the magnetic field of the guidance coil Z1, and is smoothly moved with less friction on the intracavital surface.

As the capsule endoscope 21 advances, the magnetic field generated by the guidance coils D2 and D4 is increased in the gradient at the position of the capsule endoscope, and the pulling force is increased. Namely, the moving speed of the capsule endoscope is increased. To move the capsule endoscope 21 at a constant speed, it is necessary to keep the propulsive force constant. Therefore, the intensity of the magnetic field generated by the guidance coils D2 and D4 is gradually decreased as shown in FIG. 8(b).

As explained above, the magnetic field intensity is controlled based on the information about a position of the capsule endoscope 21, the gravity applied to the endoscope is cancelled, and the frictional force acting between the capsule endoscope 21 and intracavital tissue is decreased. By generating a gradient magnetic field inclined to the direction wanted to move the capsule endoscope 21 in the state that the gravity is cancelled, the operation of guiding the endoscope can be made easy by decreasing the resistance caused by the movement, and the endoscope can be equally moved by a magnetic field with a lower intensity.

Next, an explanation will be given to a second method of controlling an encapsulated medical device guidance system.

In this second control method, as shown in FIGS. 9(a) and (b), the intensity of a magnetic field is controlled by the number of applying an on signal with a predetermined short pulse width to a drive signal applied to the guidance coils Z1, D2 and D4 in a period over which one magnetic field is generated. According to this method, a magnetic field is generated like a pulse in each guidance coil, the intervals between the generated magnetic fields are controlled, and the intensity of each magnetic field is controlled as a result. This is realized by adding a known switching circuit to the power supply 2 for guidance coils.

With this configuration, the guidance coils Z1, D2 and D4 generate a magnetic field like a pulse, and the intensity of each magnetic field is controlled by controlling the intervals between the generated magnetic fields. By this control, the configuration of the power supply for guidance coils can be made simple. An equivalent control method can be realized by using a PWM (Pulse Width Modulation) control method, which controls the on time (pulse width).

Next, an explanation will be given to a third method of controlling an encapsulated medical device guidance system. The third control method shown in FIG. 10 realizes similar movement of the capsule endoscope 21 by driving different combinations of guidance coils, unlike the first control method. The third capsule endoscope shown in FIG. 4 is suitable for the third control method.

In the third capsule endoscope, the magnet 51 is arranged along the longitudinal axis (in the direction of the axis C) of the endoscope (with the N-pole set forward and S-pole set backward). The magnetic induction coils 52 and 53 are crossed (here, perpendicular to each other), and each induction coil is also arranged perpendicular to the magnetic lines of force of the magnet 51. Further, in the induction coils 52 and 53 in this embodiment, a wire is wound around a core made of a needle-like magnetic substance, and the capacitors 54 and 55 are connected to the induction coils. The L-component or C-component of these two induction coils 52 and 53 is adjusted to have different resonance frequencies.

In such a configuration, the direction of magnetic lines of force from the magnet 51 can be arranged to be vertical to the longitudinal direction of the induction coils 52 and 53, and the influence of the magnetic field from the magnet 51 can be reduced to minimum, and the direction of the capsule endoscope can be determined by detecting the directions of two induction coils 52 and 53.

Figure 10:
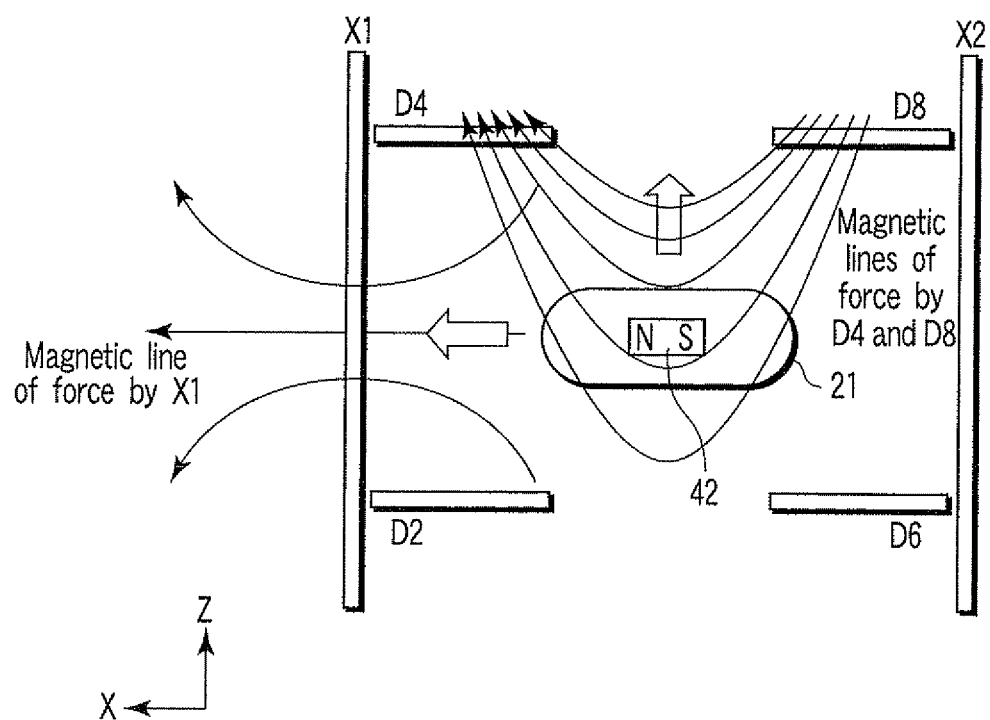
FIG. 10 is a view showing an example of a magnetic field viewed from the Y-axis direction related to guidance, for explaining a third method of controlling a encapsulated medical device guidance system.

The magnet incorporated in the capsule endoscope 21 shown in FIG. 10 is made to face the advancing direction (in the X-direction shown in FIG. 10) of the capsule endoscope 21, but the same control as shown in FIG. 7 is possible by adding a magnetic field as shown in FIG. 10. Namely, by generating a gradient magnetic field with the intensity gradually increased in the Z-axis direction (upward) by the guidance coils D4 and D8, an attractive force opposed to gravity is formed, and a gradient magnetic field is generated with the intensity gradually increased in the X-direction from the guidance coil X (to the left side in the drawing), and the capsule endoscope 21 can be moved in the X-direction with the gravity decreased.

Next, an explanation will be given on the posture control of the capsule endoscope 21 by referring to FIG. 11.

An explanation will be given by using the magnetic guidance unit 1 shown in FIG. 1 and the third capsule endoscope 21 shown in FIG. 4.

An explanation will be given on the posture of the capsule endoscope 21 inclined from the horizontal, for example, the tilt position where the distal end portion of the endoscope is raised, and the proximal end portion contacts the digestive organs.

To adopt this position, a first magnetic field advancing upward in the Z-axis direction is generated by using the guidance coils Z1 and Z2 among fourteen guidance coils X1, X2, Y, Y2, Z1 Z2, and D1-D8, and a second magnetic field advancing to the left side in the drawing (FIG. 11) in the X-axis direction is generated by using the guidance coils X1, and X2. It is possible to inline only the first magnetic field generated by the guidance coils Z1 and Z2. A magnetic field synthesized from the first and second magnetic fields is an external magnetic field H in FIG. 11. However, as gravity is applied to the capsule endoscope 21, the direction to the capsule endoscope 21 does not become parallel to the external magnetic field H, the capsule endoscope 21 turn to the down direction. At this time, magnetization of the magnet 42 is assumed to be M, the external magnetic field is assumed to be H, the angle formed by M and H is assumed to be δ, the mass of the capsule endoscope 21 is assumed to be m, the gravity acceleration is assumed to be g, the angle formed by the Z-direction and the direction of the capsule endoscope 21 is assumed to be θ, the gravity of the capsule endoscope 21 is assumed to be G, the pivot of rotation when the capsule endoscope 21 is faced upward and θ is changed is assumed to be P, and the distance from the pivot P is assumed to be 1. At this time, for simplicity, the pivot P can be the center of the semiround shape of the exterior end portion on the side not provided with the imaging optics 26 in the capsule endoscope 21. By using the above-defined items, the following equation is established.

$$\delta = \sin^{-1}\left(\frac{mgl\sin\theta}{H \cdot M}\right) \quad \text{[Equation 1]}$$

According to the equation, a magnetic field may be added in the direction of Θ=θ−δ to direct the capsule endoscope 21 to the θ direction (to adopt a target posture). A magnetic field generated by the guidance coil group is controlled in this way. Concretely, a target posture is set, and the dynamic torque estimation unit provided in the control unit estimates a torque (dynamic torque) generated in the capsule endoscope 21, based on the large of gravity applied to the capsule endoscope 21 in the target posture. Then, when the capsule endoscope 21 adopts the target posture, the control unit calculates a magnetic field to generate a magnetic torque proportional to the estimated dynamic torque. (This magnetic field is directed to the direction Θ.)

By adding this magnetic field in the Θ direction, a magnetic torque is generated in the magnet 42 built into the capsule endoscope 21, and a torque (dynamic torque) generated in the capsule endoscope 21 by the gravity applied to the capsule endoscope 21 is proportional to the magnetic torque when the capsule endoscope 21 faces the direction θ. Therefore, the capsule endoscope 21 can be directed to a desired direction (the direction θ) without being influenced by gravity.

When a magnetic field is formed in the guidance coil X1 to generate an attractive force to pull in the forward direction, for example, while the capsule endoscope 21 is existing in the tilt position in such a magnetic field, the capsule endoscope 21 is moved forward while keeping the tilt position in the state that only the proximal end portion of the capsule case 23 contacts the wall of the digestive organs. By moving in this way, the capsule endoscope easily rides over an uneven spot on a pathway on the wall of the digestive organs. Further, by superposing a magnetic field or an electric field to cancel gravity by using the guidance coil Z1, the capsule endoscope can be moved with a decreased frictional force.

When water remains in the intracavital, buoyancy equivalent to gravity may be generated. In such a state, the capsule endoscope is inclined to a position with the side having a heavier specific gravity to water faced downward, and imaging of a desired part may become difficult. Therefore, in this embodiment, a desired position is realized by forming magnetic fields by the guidance coil group.

Only the difference from the above conditions is that the capsule endoscope 21 is floated on the water. In this case, buoyancy in addition to gravity is applied to the capsule endoscope 21. The buoyancy generates a torque (a dynamic torque) to be applied to the capsule endoscope, as is the gravity.

Figure 12:
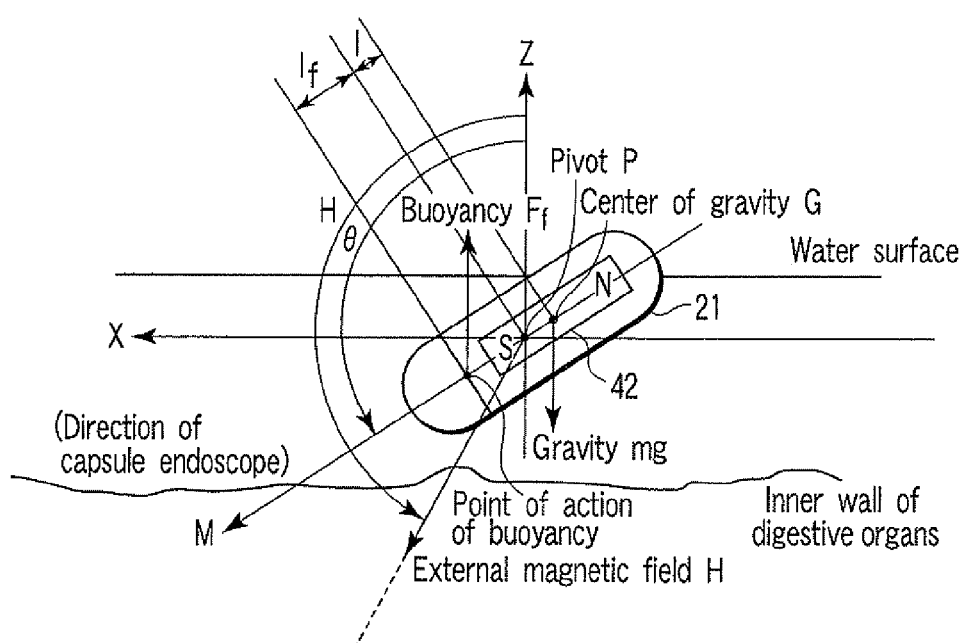
FIG. 12 is a view for explaining a posture control considering buoyancy in a capsule endoscope.

Therefore, the torque generated by the buoyancy is also determined in addition to the torque generated by the dynamic torque estimation unit generates in the capsule endoscope 21, the control unit calculates a magnetic field to generate a magnetic torque proportional to these two torques, and generates that magnetic field, thereby the capsule endoscope 21 can be controlled to adopt a target posture even if the capsule endoscope 21 is floated on the water. For example, when water remains on the inner wall of the digestive organs and the distal end of the capsule endoscope 21 is floated, the induction coils X1/X2 and Z1/Z2 are used to incline the capsule endoscope to the tilt position as shown in FIG. 12. Namely, the induction coils Z1 and Z2 are used to form a third magnetic field toward the Z-axis downward, and the induction coils Z1 and Z2 are used to form a fourth magnetic field toward the X-axis direction.

By these magnetic fields, even if the distal end or proximal end portion of the capsule endoscope 21 is floated by buoyancy, the position of the capsule endoscope can be easily controlled and a desired part can be imaged. Further, in this embodiment, the capsule endoscope 21 contains a magnet, but the magnet may be replaced by a magnetic substance having an axis easily magnetized. In this case, the magnetic substance is shaped like a stick or a plate. Further, the magnetic substance may be a battery to supply power to the capsule endoscope 21. The magnetic substance may also be a shield to protect the electronic circuit built into the capsule endoscope 21.

Further, even if the capsule endoscope 21 is not floated on the water but immersed in water, more exact posture control is possible by using the above scheme. Now, the configuration of the dynamic torque estimation unit will be explained more concretely.

The dynamic torque estimation unit stores necessary items among the weight of the capsule endoscope 21 m×g, the center of gravity of the capsule endoscope 21, the position P of a pivot as a center of rotation of the capsule endoscope 21 (refer to FIGS. 11 and 12), the distance l from the pivot as a center of rotation of the capsule endoscope 21 to the position of the center of gravity (refer to FIG. 11), the buoyancy Ff (refer to FIG. 12), and the distance lf from an point of action of the buoyancy to the position P of the pivot as the center of rotation of the capsule endoscope 21 (refer to FIG. 12), as basic physical characteristics of the capsule endoscope 21.

Further, in the state that the capsule endoscope 21 is floated on the water, the capsule endoscope 21 projects from the water surface, and the part of the capsule endoscope 21 projected from the water surface is also changed if the posture of the capsule endoscope 21 is changed further. This means that the part of the capsule endoscope 21 is changed by the buoyancy, the distance from the position P of the pivot as a center of rotation of the capsule endoscope 21 to the point of action of buoyancy, and the posture of the capsule endoscope 21, stored in the dynamic torque estimation unit.

Therefore, it is desirable to hold the information about the buoyancy, the distance from the position P of the pivot as a center of rotation of the capsule endoscope 21 to the point of action of buoyancy, and the position of the pivot as a center of rotation of the capsule endoscope, as a lookup table corresponding to the function of the posture of the capsule endoscope 21, or the posture of the capsule endoscope 21. By these information and information about the object posture, the dynamic torque estimation unit calculates a dynamic torque to be applied to the capsule endoscope 21 when the capsule endoscope 21 adopts the target posture. This calculation is made by the following formulas.

Figure 11:
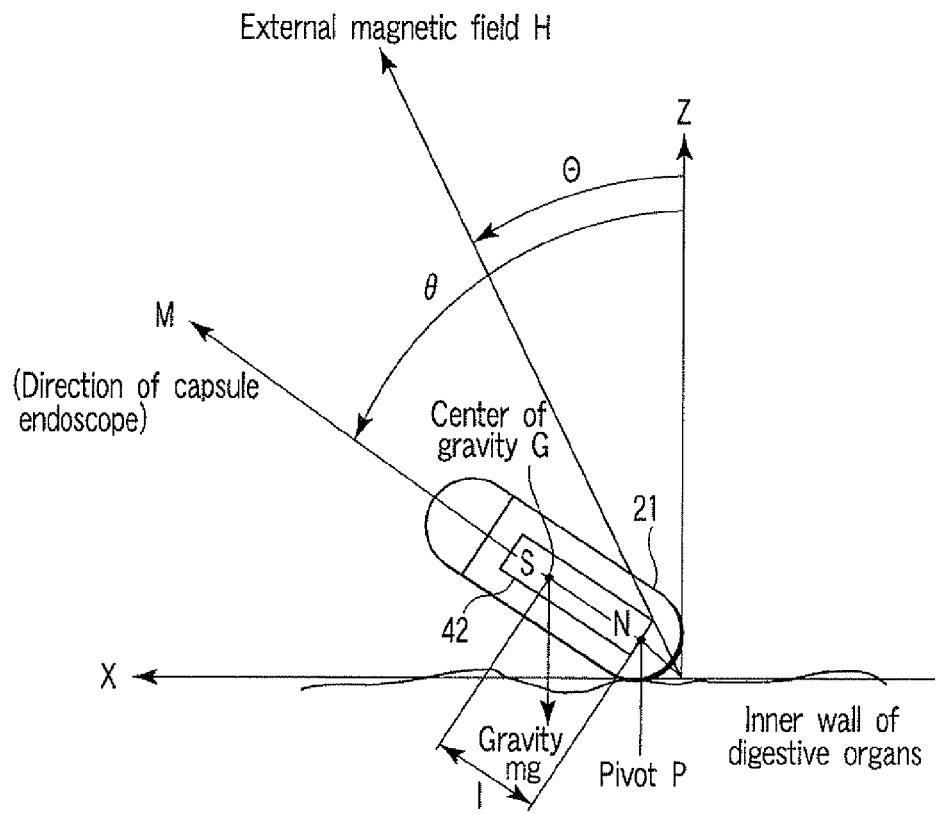
FIG. 11 is a view for explaining a posture control considering gravity in a capsule endoscope.

In case of FIG. 11:
Torque by gravity mgl×cos(θ)
Torque by gravity 0
In case of FIG. 12:
Torque by gravity mgl×cos(θ)
Torque by gravity −Ff if sin(θ)

When the difference between the position of the pivot as a center of rotation of the capsule endoscope 21 and the center of gravity position of the capsule endoscope 21 is vary small (e.g., 2 mm or less, preferably approximately 1 mm), the torque by gravity may be regarded as 0. In this case, the pivot as a center of rotation of the capsule endoscope 21 may be considered to be the center of gravity of the capsule endoscope, and the calculation can be simplified.

When the capsule endoscope 21 is positioned under the water surface as shown in FIG. 11:
Torque by gravity mgl×cos(θ)
Torque by gravity −Ff×lf×sin(θ)

The value of the torque determined by the above calculation is sent to the control unit. When the capsule endoscope 21 adopts the target posture, the control unit calculates a magnetic field to generate a magnetic torque proportion to the estimated dynamic torque.

By generating such a magnetic field, the control unit can control the capsule endoscope to a target posture. These conditions surrounding the capsule endoscope 21 can be selected by the operator by providing a selector to input the control unit.

Next, the control unit will be explained in detail. The control unit stores the characteristics of the magnet 42 built into the capsule endoscope 21, concretely a magnet magnetizing strength M, and a posture information of magnet in the capsule endoscope 21. In this embodiment, the magnet magnetizing direction is identical to the major axis of the capsule endoscope 21, but the posture of the capsule endoscope 21 can be controlled by referring the above magnet posture information, even if the magnet adopts a different posture.

As explained herein, the encapsulated medical device according to the embodiments of the invention, the posture of the medical device can be easily and accurately controlled. In particular, as an effect of the encapsulated medical device, it is possible to image a desired part by easily and accurately controlling the posture.

The present invention is not limited to the described embodiments. Numerous modifications are possible without departing from the substance of the invention. Not all components of the embodiments may be mounted, and only the executable components may be used.

What is claimed is:

1. An encapsulated medical device guidance system comprising:
    an encapsulated medical device having an internal biological information acquisition unit to acquire internal biological information, a communication unit to output the acquired internal biological information to the outside as an output signal, and a magnet;
    a magnetic field generator which acts on the magnet, and generates a magnetic field for controlling at least one of the position and posture of the encapsulated medical device;
    a control unit to control the magnetic field generator; and
    a target posture setting unit to set a desired target posture of the encapsulated medical device,
    wherein the control unit has a dynamic torque estimation unit to estimate a dynamic torque to be applied to the encapsulated medical device in order to achieve or maintain the target posture, the dynamic torque estimation unit estimating the necessary dynamic torque based on gravity that acts on the encapsulated medical device, buoyancy that acts when the encapsulated medical device is floated on water or immersed in water, on the encapsulated medical device, and preliminarily stored characteristics of the encapsulated medical device consisting of at least one of: a weight, a center position of gravity, a pivot position as a center of rotation, a distance between the center position of gravity and the pivot position, buoyancy, and a distance between the pivot position and an action point of the buoyancy, and
    the control unit controls a magnetic field generated from the magnetic field generator so that a magnetic torque generated by applying a magnetic field generated by the magnetic field generator to the magnet becomes substantially proportional to a dynamic torque estimated by the dynamic torque estimation unit.

2. The system according to claim 1, wherein the dynamic torque estimation unit estimates a dynamic torque applied to the encapsulated medical device by buoyancy applied to the encapsulated medical device.

3. The system according to claim 1, wherein the magnet is a magnet.

4. The system according to claim 1, wherein the magnet is a battery.

5. The system according to claim 1, wherein the dynamic torque estimation unit has at least one of information about the center of gravity of the encapsulated medical device, the weight of the encapsulated medical device, the pivot as a center of rotation of the encapsulated medical device, the distance from a point of action of buoyancy to the pivot, and the strength of buoyancy of the encapsulated medical device.

6. The system according to claim 1, wherein the dynamic torque estimation unit has at least one of information about the distance from a point of action of buoyancy of the encapsulated medical device to the pivot, the strength of buoyancy of the encapsulated medical device, and the pivot as a center of rotation of the encapsulated medical device, as a variate to the posture of the encapsulated medical device.

7. The system according to claim 5, wherein the dynamic torque estimation unit estimates a dynamic torque by taking a spot in the vicinity of one end portion of the encapsulated medical device as a pivot which is a center of rotation of the encapsulated medical device.

8. The system according to claim 5, wherein the dynamic torque estimation unit estimates a dynamic torque by taking the center of gravity of the encapsulated medical device as a pivot which is a center of rotation of the encapsulated medical device.

9. The system according to claim 3, wherein the control unit has at least one of information about the strength of magnetization of the magnet and the posture of the magnet in the encapsulated medical device.

10. The system according to claim 1, wherein the magnetic field generator has at least two guidance coils to generate magnetic fields in different directions to the encapsulated medical device.

11. The system according to claim 1, wherein the magnetic field generator generates also a magnetic field to pull the encapsulated medical device.

12. The system according to claim 1, wherein the control unit preliminarily stores magnet characteristics including at least one of a magnetizing strength of the magnet in the encapsulated medical device and posture information of the magnet in the encapsulated medical device, and the dynamic torque estimation is performed based on the magnet characteristics.

\* \* \* \* \*